(12) United States Patent
Joji

(10) Patent No.: US 12,081,810 B2
(45) Date of Patent: Sep. 3, 2024

(54) CONTENT DISPLAY APPARATUS, CONTENT DISPLAY METHOD, AND STORAGE MEDIUM STORING PROGRAM

(71) Applicant: JOLLY GOOD Inc., Tokyo (JP)

(72) Inventor: Kensuke Joji, Tokyo (JP)

(73) Assignee: JOLLY GOOD INC., Tokyo (JP)

( * ) Notice: Subject to any disclaimer, the term of this patent is extended or adjusted under 35 U.S.C. 154(b) by 11 days.

(21) Appl. No.: 17/820,884

(22) Filed: Aug. 19, 2022

(65) Prior Publication Data
US 2023/0010797 A1 Jan. 12, 2023

Related U.S. Application Data

(63) Continuation of application No. PCT/JP2021/006109, filed on Feb. 18, 2021.

(30) Foreign Application Priority Data

Feb. 26, 2020 (JP) ................................ 2020-030723

(51) Int. Cl.
*H04N 21/232* (2011.01)
*H04N 21/218* (2011.01)

(52) U.S. Cl.
CPC ..... *H04N 21/232* (2013.01); *H04N 21/21805* (2013.01)

(58) Field of Classification Search
CPC ....................... H04N 21/232; H04N 21/21805
See application file for complete search history.

(56) References Cited

U.S. PATENT DOCUMENTS

| 2012/0127157 A1 | 5/2012 | Adler et al. |
| 2016/0220163 A1 | 8/2016 | Yamada et al. |
| 2018/0211285 A1* | 7/2018 | Todasco ............ G06Q 30/0277 |
| 2021/0314645 A1* | 10/2021 | Everett ............ H04N 21/25891 |

FOREIGN PATENT DOCUMENTS

| JP | 2012110717 A | 6/2012 |
| JP | 201430657 A | 2/2014 |
| JP | 2016146173 A | 8/2016 |
| JP | 201996283 A | 6/2019 |

* cited by examiner

*Primary Examiner* — Nnenna N Ekpo
(74) *Attorney, Agent, or Firm* — HAUPTMAN HAM, LLP

(57) ABSTRACT

A content display apparatus includes: a state identifying part that identifies a state of a viewer who is to view content; an image data selecting part that selects a plurality of pieces of image data from a plurality of image data candidates on the basis of the state of the viewer identified by the state identifying part; a content generating part that generates state improvement content for improving the state of the viewer by determining an order in which to display the plurality of pieces of image data; and a display control part that causes a display part viewed by the viewer U to display the state improvement content.

21 Claims, 6 Drawing Sheets

CONTENT DISPLAY APPARATUS, CONTENT DISPLAY METHOD, AND STORAGE MEDIUM STORING PROGRAM

CROSS-REFERENCE TO RELATED APPLICATIONS

The present application is a continuation application of International Application number PCT/JP2021/006109, filed on Feb. 18, 2021, which claims priority under 35 U.S.C § 119(a) to Japanese Patent Application No. 2020-030723, filed on Feb. 26, 2020. The contents of these applications are incorporated herein by reference in their entirety.

BACKGROUND OF THE INVENTION

The present disclosure relates to a content display apparatus for displaying content, a content display method, and a storage medium storing a program in a non-transitory manner.

Conventionally, there has been known a technique of evaluating a fatigue state of a person and outputting an image indicating a result of the evaluation. Japanese Unexamined Patent Application Publication No. 2019-096283 discloses a health guidance support device that outputs an image indicating a countermeasure against symptoms related to fatigue.

In a case of a person having a mental disorder, such as depression or anxiety, it is necessary to periodically have a consultation with a psychologist for improving symptoms, but there has been a problem that the symptoms cannot be improved since the consultation cannot be held.

BRIEF SUMMARY OF THE INVENTION

Accordingly, the present disclosure focuses on this point, and its object is to provide a content display apparatus, a content display method, and a storage medium storing a program in a non-transitory manner, which makes it possible to improve a state of a person having a health problem.

A content display apparatus of the first aspect of the present disclosure is a content display apparatus for displaying content, the content display apparatus includes a state identifying part that identifies a state of a viewer who is to view the content, an image data selecting part that selects a plurality of pieces of image data from a plurality of image data candidates on the basis of the state of the viewer identified by the state identifying part, a content generating part that generates state improvement content for improving the state of the viewer by determining an order in which to display the plurality of pieces of image data, and a display control part that causes a display part viewed by the viewer to display the state improvement content.

A content display method of the second aspect of the present disclosure, executed by a computer, includes the steps of identifying a state of a viewer who is to view content using a content display apparatus, selecting a plurality of pieces of image data from a plurality of image data candidates on the basis of the identified state of the viewer, generating state improvement content for improving the state of the viewer by determining an order in which to display the plurality of pieces of image data, and causing a display part viewed by the viewer to display the content.

A storage medium of the third aspect of the present disclosure stores, in a non-transitory manner, a program for causing a computer to function as a state identifying part that identifies a state of a viewer who is to view content using a content display apparatus, an image data selecting part that selects a plurality of pieces of image data from a plurality of image data candidates on the basis of the state of the viewer identified by the state identifying part, a content generating part that generates state improvement content for improving the state of the viewer by determining an order in which to display the plurality of pieces of image data, and a display control part that causes a display part viewed by the viewer to display the state improvement content.

DETAILED DESCRIPTION OF THE INVENTION

Hereinafter, the present disclosure will be described through exemplary embodiments, but the following exemplary embodiments do not limit the invention according to the claims, and not all of the combinations of features described in the exemplary embodiments are necessarily essential to the solution means of the invention.

Outline of the Content Display Apparatus 1

Figure 1:
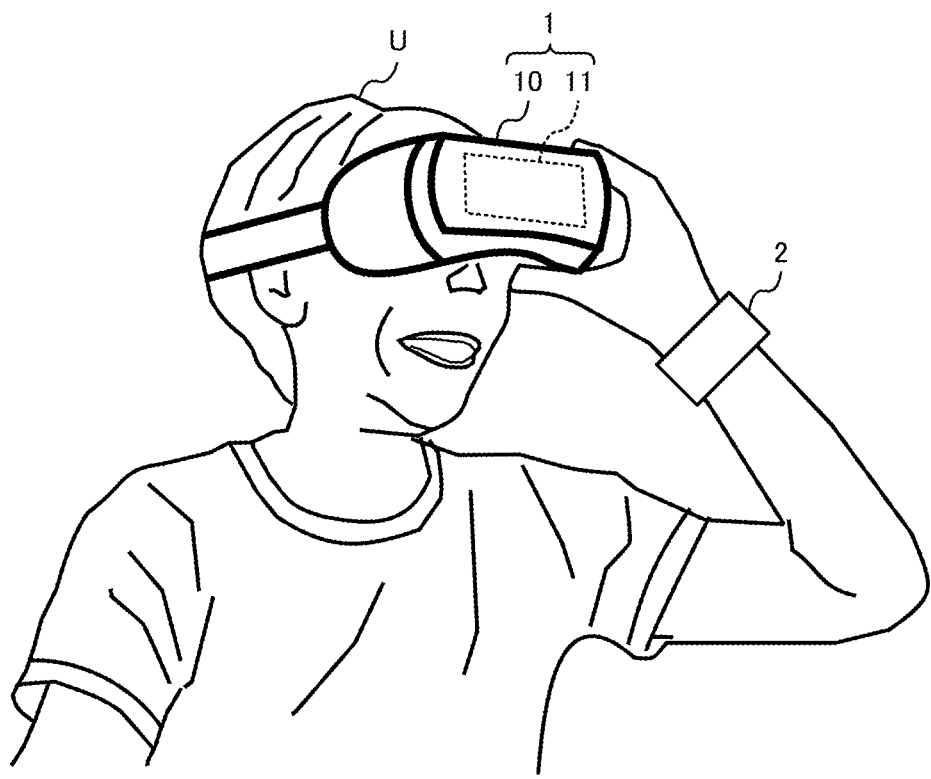
FIG. 1 illustrates an outline of a content display apparatus 1.

FIG. 1 illustrates an outline of a content display apparatus 1. The content display apparatus 1 is an apparatus for displaying content that can be viewed by a viewer U. The viewer U is a person who needs to check or improve his/her health condition, and may have a health problem, like a person who may have a mental disorder, for example. The content display apparatus 1 identifies a state of the viewer U, and displays content including an image that can be effective for improving an identified symptom. The image included in the content is a 360-degree video that can provide the viewer U with virtual reality, for example, but the shape or size of the image included in the content is arbitrary. When the viewer U needs to improve his/her health condition, the viewer U can improve his/her health condition by viewing the content displayed by the content display apparatus 1.

The content display apparatus 1 includes a housing 10 and a display part 11. The housing 10 is in a goggle shape, for example. The shape of the housing 10 is any shape as long as the viewer U can see the content displayed by the content display apparatus 1. The display part 11 is a display provided on a side to be viewed by the viewer U wearing the housing 10, and displays the content.

The viewer U shown in FIG. 1 wears a biometric information measuring device 2 on his/her wrist. The biometric information measuring device 2 is a device that measures biometric information indicating a state of the viewer U's body (e.g., a pulse, blood pressure, body temperature, and an amount of sweating), and notifies the content display apparatus 1 of the measured biometric information. The biometric information measuring device 2 notifies the content display apparatus 1 of the biometric information by a wireless communication means, such as Bluetooth Low Energy (BLE, Bluetooth is a registered trademark), for example.

Figure 2:
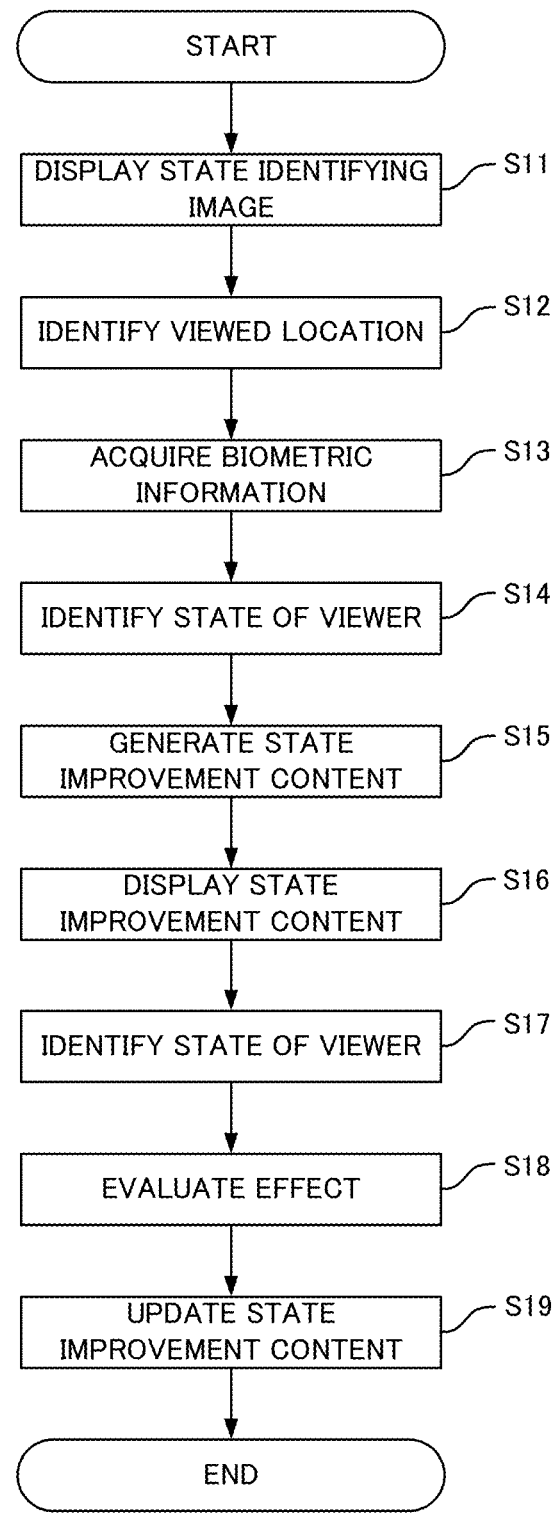
FIG. 2 is a flowchart showing an outline of operations of the content display apparatus 1.

FIG. 2 is a flowchart showing an outline of operations of the content display apparatus 1. The flowchart shown in FIG. 2 starts at the time when the power of the content display apparatus 1 has been turned on and a processor included in the content display apparatus 1 has started executing a predetermined program.

The content display apparatus 1 first displays a state identifying image for identifying the state of the viewer U (S11). The state identifying image is an image that is generated in advance so that the state of the viewer U can be identified on the basis of the position of the line of sight of the viewer U viewing the state identifying image, and the state of the viewer U's body. As an example, the state identifying image includes an image of a wider area than the area of the display part 11. The state identifying image is an image captured by a 360-degree camera, for example.

The content display apparatus 1 includes a device that detects movement of the content display apparatus 1, such as an angular velocity sensor (a gyro sensor) or an acceleration sensor. The content display apparatus 1 specifies an amount of movement from a reference position that is a position of the content display apparatus 1 at the time when the content display apparatus 1 was activated, and displays an image corresponding to the specified amount of movement on the display part 11. That is, when the viewer U changes the direction of his/her face while wearing the content display apparatus 1, the image displayed on the display part 11 changes.

The content display apparatus 1 identifies a location that the viewer U is looking at (i.e., a viewed location) in the state identifying image (S12). A method of identifying the viewed location by the content display apparatus 1 will be described later in detail.

Further, the content display apparatus 1 acquires biometric information measured by the biometric information measuring device 2 (S13). As an example, the content display apparatus 1 identifies the state of the viewer U on the basis of the identified viewed location and biometric information of the viewer U (S14).

Figure 3A:
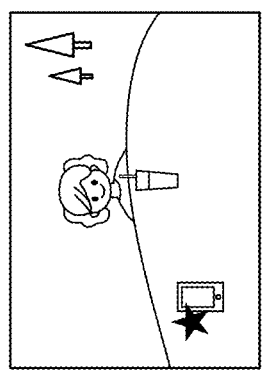
FIG. 3A shows a relationship among a state identifying image, a viewed location of a viewer U, and biometric information of the viewer U.
Figure 3A:
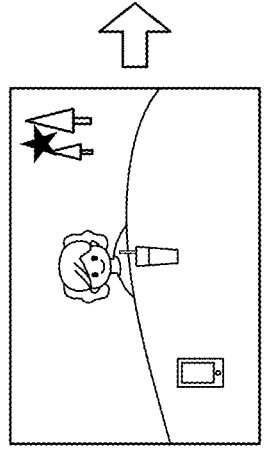
Figure 3A:
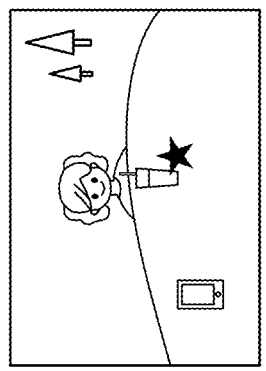
Figure 3B:
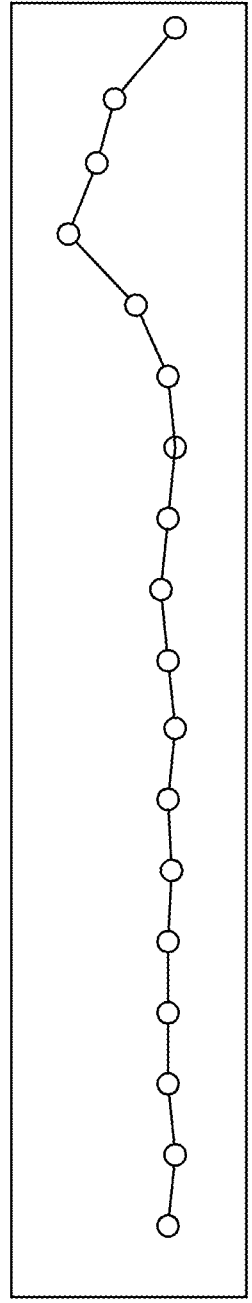
FIG. 3B shows the relationship among the state identifying image, the viewed location of the viewer U, and the biometric information of the viewer U.

FIGS. 3A and 3B show a relationship among the state identifying image, the viewed location of the viewer U, and the biometric information of the viewer U. FIG. 3A shows the state identifying image, and FIG. 3B shows a change in the biometric information (for example, a pulse) of the viewer U over time. A star (*) in FIG. 3A indicates the viewed location of the viewer U. In the example shown in FIGS. 3A and 3B, the biometric information changes while the viewer U is looking at a drink. The content display apparatus 1 identifies a physical and mental state of the viewer U in this manner, on the basis of a relationship between a target looked at by the viewer U and the biometric information.

Subsequently, the content display apparatus 1 generates state improvement content for improving the state of the viewer U on the basis of the identified physical and mental state of the viewer U (S15). The content display apparatus 1 refers to data indicating a relationship among the physical and mental state, types of images to be included in the state improvement content, order of images, and display time of each image, for example, thereby determining the types of images, the order of images, and the display time of each image suitable for the identified physical and mental state of the viewer U. The content display apparatus 1 generates state improvement content including images of the determined type, in the determined order, and for the determined time, and then displays the generated state improvement content on the display part 11 (S16).

After the viewer U viewed the state improvement content, the content display apparatus 1 identifies the state of the viewer U again (S17). The content display apparatus 1 may identify the state of the viewer U using the state identifying image used in the step S11, or may identify the state of the viewer U using another method. The content display apparatus 1 evaluates an effect of the viewer U viewing the state improvement content by comparing the state of the viewer U identified again with the state of the viewer U identified in the step S14 (S18).

The content display apparatus 1 updates the state improvement content on the basis of the evaluation result (S19). Although details will be described later, if the state of the viewer U is not improved, the content display apparatus 1 changes the state improvement content to be displayed on the display part 11, for example. If the state of the viewer U is improved, the content display apparatus 1 causes the display part 11 to display the same or similar content as the content viewed by the viewer U, or causes the display part 11 to display new state improvement content suitable for the improved state of the viewer U.

Hereinafter, a configuration and operations of the content display apparatus 1 will be described in detail.

Configuration of the Content Display Apparatus 1

Figure 4:
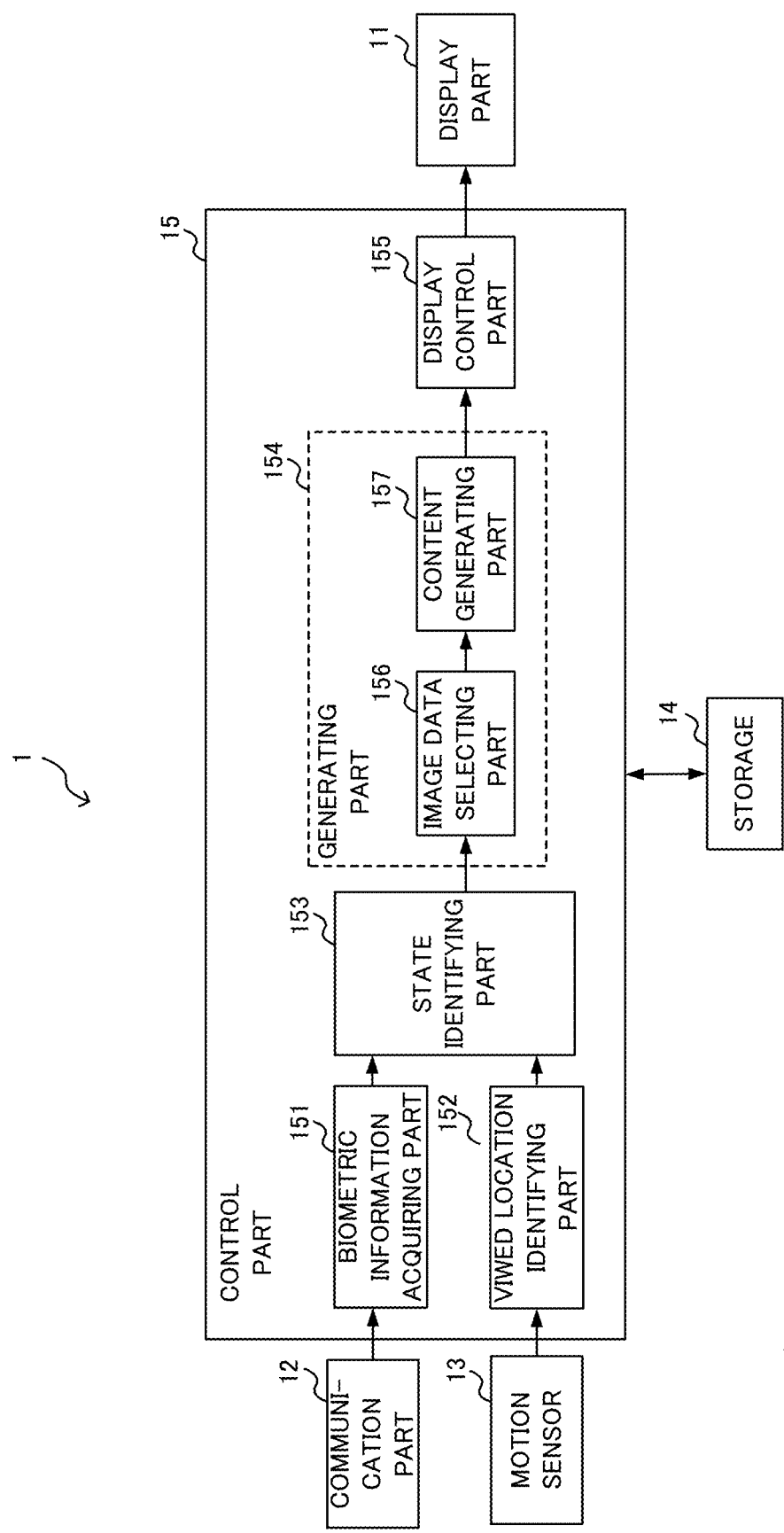
FIG. 4 shows a configuration of the content display apparatus 1.

FIG. 4 shows a configuration of the content display apparatus 1. The content display apparatus 1 includes a display part 11, a communication part 12, a motion sensor 13, a storage 14, and a control part 15. The control part 15 includes a biometric information acquiring part 151, a viewed location identifying part 152, a state identifying part 153, a generating part 154, and a display control part 155. The generating part 154 includes an image data selecting part 156 and a content generating part 157.

The communication part 12 is a communication interface for transmitting and receiving data to and from other devices. The communication part 12 is a communication controller such as Wi-Fi (a registered trademark) or BLE. The communication part 12 receives biometric information generated by the biometric information measuring device 2, and notifies the biometric information acquiring part 151 of the received biometric information, for example.

The motion sensor 13 is a sensor that detects movement of the content display apparatus 1, and is an acceleration sensor, for example. The motion sensor 13 notifies the viewed location identifying part 152 of information indicating the detected acceleration.

The storage 14 includes a storage medium, such as a Read Only Memory (ROM) and a Random Access Memory (RAM). The storage 14 stores a plurality of image data candidates used for forming content displayed on the display part 11. The storage 14 stores a plurality of pieces of image data downloaded from an external server via the communication part 12, as the plurality of image data candidates, for example. Image data identification information and content of the image indicated by the image data are associated with each of the plurality of image data candidates. The storage 14 further stores a program executed by the control part 15.

The control part 15 includes a Central Processing Unit (CPU), for example. By executing a program stored in the storage 14, the control part 15 functions as the biometric information acquiring part 151, the viewed location identifying part 152, the state identifying part 153, the generating part 154, the display control part 155, the image data selecting part 156, and the content generating part 157.

The biometric information acquiring part 151 acquires biometric information from the communication part 12. The biometric information acquiring part 151 acquires biometric information of the viewer U while the viewer U is looking at the state identifying image. The biometric information acquiring part 151 inputs the acquired biometric information to the state identifying part 153. In this specification, a state identifying image used for identifying the state of the viewer U before the viewer U views state improvement content may be referred to as the first state identifying image, and a state identifying image used for identifying the state of the viewer U after the viewer U has viewed the state improvement content may be referred to as the second state identifying image.

The viewed location identifying part 152 identifies a location that the viewer U is looking at in the state identifying image. The content display apparatus 1 identifies the direction of the viewer U's line of sight by detecting the position of the viewer U's pupil, and identifies a location corresponding to the direction of the line of sight as a viewed location, for example. When an area that can be viewed by the viewer U in the state identifying image changes due to the viewer U moving his/her face, the content display apparatus 1 may identify the central position of the state identifying image displayed on the display part 11 as the viewed location, assuming that the viewer U is looking at the center of the display part 11. The viewed location identifying part 152 inputs the identified viewed location to the state identifying part 153.

The state identifying part 153 identifies the state of the viewer U, who is to view the content. The state identifying part 153 identifies the state of the viewer U on the basis of a viewed location, which is a location that the viewer U is looking at in the state identifying image displayed on the display part 11 by the display control part 155, for example. The state identifying part 153 may identify the state of the viewer U on the basis of the content of the image displayed at the viewed location (e.g., the content of a subject). As described above, the state identifying part 153 may improve the accuracy of identifying the state of the viewer U by identifying the state of the viewer on the basis of a relationship between the viewed location and the biometric information acquired by the biometric information acquiring part 151 at the time when the viewer U is viewing this viewed location.

The generating part 154 generates state improvement content for improving the state of the viewer U on the basis of the state of the viewer U identified by the state identifying part 153. In the present specification, state improvement content generated first by the generating part 154 is referred to as the first state improvement content (corresponding to the first content).

The display control part 155 causes various types of information to be displayed on the display part 11 viewed by the viewer U. The display control part 155 first causes the display part 11 to display a state identifying image for identifying the state of the viewer U. Then, the display control part 155 causes the display part 11 to display state improvement content generated by the generating part 154.

The generating part 154 includes the image data selecting part 156 and the content generating part 157 in order to generate state improvement content. The image data selecting part 156 selects a plurality of pieces of image data from a plurality of image data candidates on the basis of the state of the viewer U identified by the state identifying part 153. The plurality of image data candidates are image data downloaded from an external server via the communication part 12, for example. The image data selecting part 156 selects a plurality of pieces of image data suitable for improving the state of the viewer U.

The image data selecting part 156 may further select a plurality of pieces of image data on the basis of the attributes (for example, sex, age, personality, and hobby) of the viewer U acquired via the communication part 12. If the viewer U is male and his hobby is playing golf, the image data selecting part 156 selects image data with a female professional golfer, for example. The content generating part 157 generates state improvement content by determining the order in which to display the selected plurality of pieces of image data.

Figure 5:
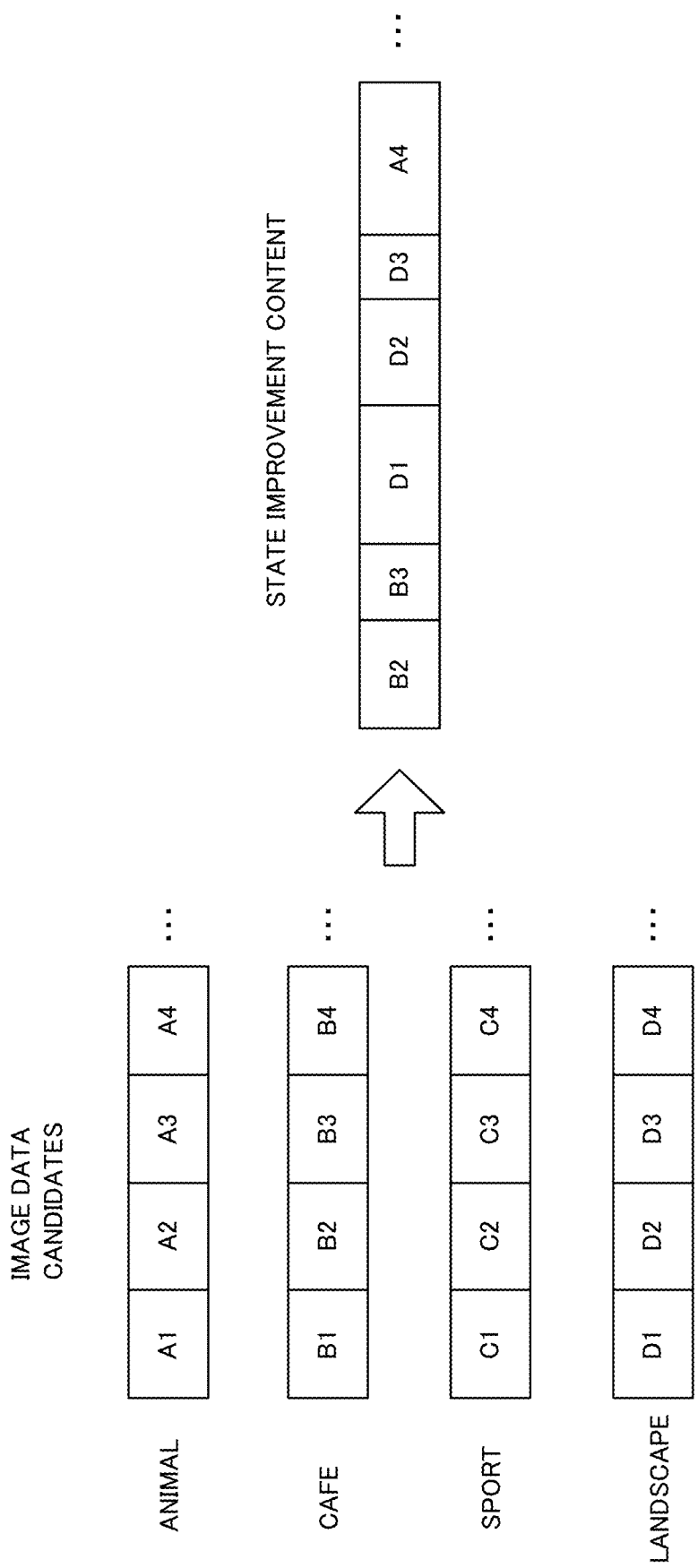
FIG. 5 illustrates a method in which a generating part 154 generates state improvement content.

FIG. 5 illustrates a method in which the generating part 154 generates state improvement content. In FIG. 5, image data candidates A1 to A4 related to an animal, image data candidates B1 to B4 related to a cafe, image data candidates C1 to C4 related to a sport, and image data candidates D1 to D4 related to a landscape are shown as a plurality of image data candidates.

In an example shown in FIG. 5, the image data selecting part 156 selects A4, B2, B3, D1, D2, and D3 from the plurality of image data candidates. Then, the content generating part 157 generates the state improvement content by determining the order of the plurality of image data candidates selected by the image data selecting part 156 such that more therapeutic effects are expected. In the example shown in FIG. 5, the content generating part 157 generates state improvement content by arranging the selected image data candidates in the order of B2, B3, D1, D2, D3, A4.

The content generating part 157 may provide the display control part 155 with, as state improvement content, one piece of data obtained by combining a plurality of pieces of image data, or may provide the display control part 155 with state improvement content by sequentially inputting a plurality of pieces of image data to the display control part 155. The content generating part 157 may acquire a plurality of pieces of image data to be provided to the display control part 155 as state improvement content, from an external server via the communication part 12, and may provide the display control part 155 with the acquired plurality of pieces of image data in the determined order.

The content generating part 157 may determine a time length of each of a plurality of pieces of image data on the basis of the state of the viewer U. In this case, the content generating part 157 uses a portion corresponding to a first time of a piece of the first image data, which is considered to directly lead to improvement of the state of the viewer U, and uses a portion corresponding to a second time, which is shorter than the first time of the other piece of the second image data. In the example shown in FIGS. 5, D1 and A4 are longer than other image data, and B3 and D3 are shorter than other image data. The content generating part 157 may continuously display the first image data and the second image data by providing the display control part 155 with the second image data before the first time passes after providing the display control part 155 with the first image data.

For example, when the state of the viewer U is nervous, the content generating part 157 determines that the first time portion of image data that can relax the viewer U is to be used as the first image data. Then, the content generating part 157 uses the second time portion of image data that attracts the viewer U's interest as the second image data, and arranges the first image data after the second image data, thereby generating the state improvement content. The content generating part 157 generates such state improvement content. This enables the viewer U to improve his/her state by viewing the second image data after starting to view the first image data with interest.

Feedback of Therapeutic Effect

Incidentally, in a case where state improvement content viewed by the viewer U is not suitable for therapy for the viewer U, it may be counterproductive for the viewer U to continue viewing. Accordingly, the content generating part 157 may generate the first state improvement content including image data used as the second state identifying image for identifying the state of the viewer U. For example, the display control part 155 causes the display part 11 to display state improvement content including a plurality of pieces of image data used for the therapy, for the predetermined time required to change the state of the viewer U, and then causes the display part 11 to display the second state identifying image.

While the display part 11 displays the second state identifying image, the state identifying part 153 identifies the state of the viewer U, on the basis of the biometric information acquired by the biometric information acquiring part 151 and the viewed location identified by the viewed location identifying part 152. The state identifying part 153 compares the first state of the viewer U identified on the basis of the result of the viewer U viewing the first state identifying image with the second state of the viewer U identified on the basis of the result of the viewer U viewing the second state identifying image. Thus, the state identifying part 153 determines the presence or absence of an effect caused by the viewer viewing the state improvement content, and then outputs a determination result.

Specifically, when the difference between the first state and the second state is within a predetermined range, in which it is estimated that no therapeutic effect is produced, the state identifying part 153 determines that no therapeutic effect is produced. When the difference between the first state and the second state is larger than the predetermined range, and the second state is better than the first state, the state identifying part 153 determines that a therapeutic effect is produced. When the difference between the first state and the second state is larger than the predetermined range, and the second state is poorer than the first state, the state identifying part 153 determines that an adverse effect is produced due to the viewer U viewing the first state improvement content.

The content generating part 157 generates the second state improvement content (corresponding to the second content) to be displayed, caused by the display control part 155, on the display part 11 after the first state improvement content, on the basis of the result of the comparison between the first state and the second state performed by the state identifying part 153. For example, when the state identifying part 153 determines that no therapeutic effect is produced, the content generating part 157 generates the second state improvement content that may improve the state of the viewer U and includes a plurality of pieces of image data different from a plurality of pieces of image data included in the first state improvement content. The content generating part 157 may generate the second state improvement content in which a plurality of pieces of image data included in the first state improvement content are included, in a different order or with a different length than in the first state improvement content.

When the state identifying part 153 determines that a therapeutic effect occurs, the content generating part 157 generates the second state improvement content including a plurality of pieces of image data included in the first state improvement content. The second state improvement content may be the same as the first state improvement content, or a plurality of pieces of image data included in the first state improvement content may be content included in a different order or with a different length than in the first state improvement content. The content generating part 157 may generate the second state improvement content by adding other image data that may be useful for improving the state of the viewer U, to the plurality of pieces of image data included in the first state improvement content.

When the state identifying part 153 determines that an adverse effect is produced, the content generating part 157 generates the second state improvement content that does not include a plurality of pieces of image data included in the first state improvement content. The content generating part 157 generates the second state improvement content including a plurality of pieces of image data associated with an attribute different from the attribute of the viewer U, among other image data that may be useful for improving the state of the viewer U, for example. In a case where an adverse effect is produced due to the attribute of the viewer U not being appropriately grasped, the content generating part 157 operating in this manner increases the probability of generating the second state improvement content, which is effective.

Use of Machine Learning Model

The generating part 154 may use a machine learning model to generate state improvement content having a high therapeutic effect. As an example, the machine learning model is a model created by machine learning (e.g., deep learning) so as to output a plurality of pieces of image data selected from a plurality of image data candidates when the state of the viewer U is input. The image data selecting part 156 inputs the state of the viewer U identified by the state identifying part 153 to such a machine learning model, and selects a plurality of pieces of image data output from the machine learning model.

In a case where the machine learning model is a model realized by deep learning so as to output state improvement content in which a plurality of pieces of image data selected from a plurality of image data candidates are arranged when the state of the viewer U is input, the generating part 154 may generate state improvement content by inputting the state of the viewer U identified by the state identifying part 153 to such a machine learning model.

In order to create the above-described machine learning model, the content display apparatus 1 may output, as training data, i) the state of the viewer U identified by the state identifying part 153, ii) arrangements of a plurality of pieces of image data in the state improvement content viewed by the viewer U or state improvement content, and iii) information indicating the presence or absence of a therapeutic effect produced by having the viewer U view this state improvement content, to a machine learning model creation apparatus (e.g., a computer). The training data may further be associated with the attributes of the viewer U.

The machine learning model creation apparatus performs deep learning on the basis of a large amount of training data acquired from a large number of content display apparatuses 1, thereby improving the accuracy of the content of image data suitable for the state of the viewer U, the order in which to display a plurality of pieces of image data, and the length in which each of the plurality of pieces of image data is displayed. By inputting the state of the viewer U to the machine learning model created in this manner, the generating part 154 can generate state improvement content having a high therapeutic effect.

Flow of Processing in the Content Display Apparatus 1

Figure 6:
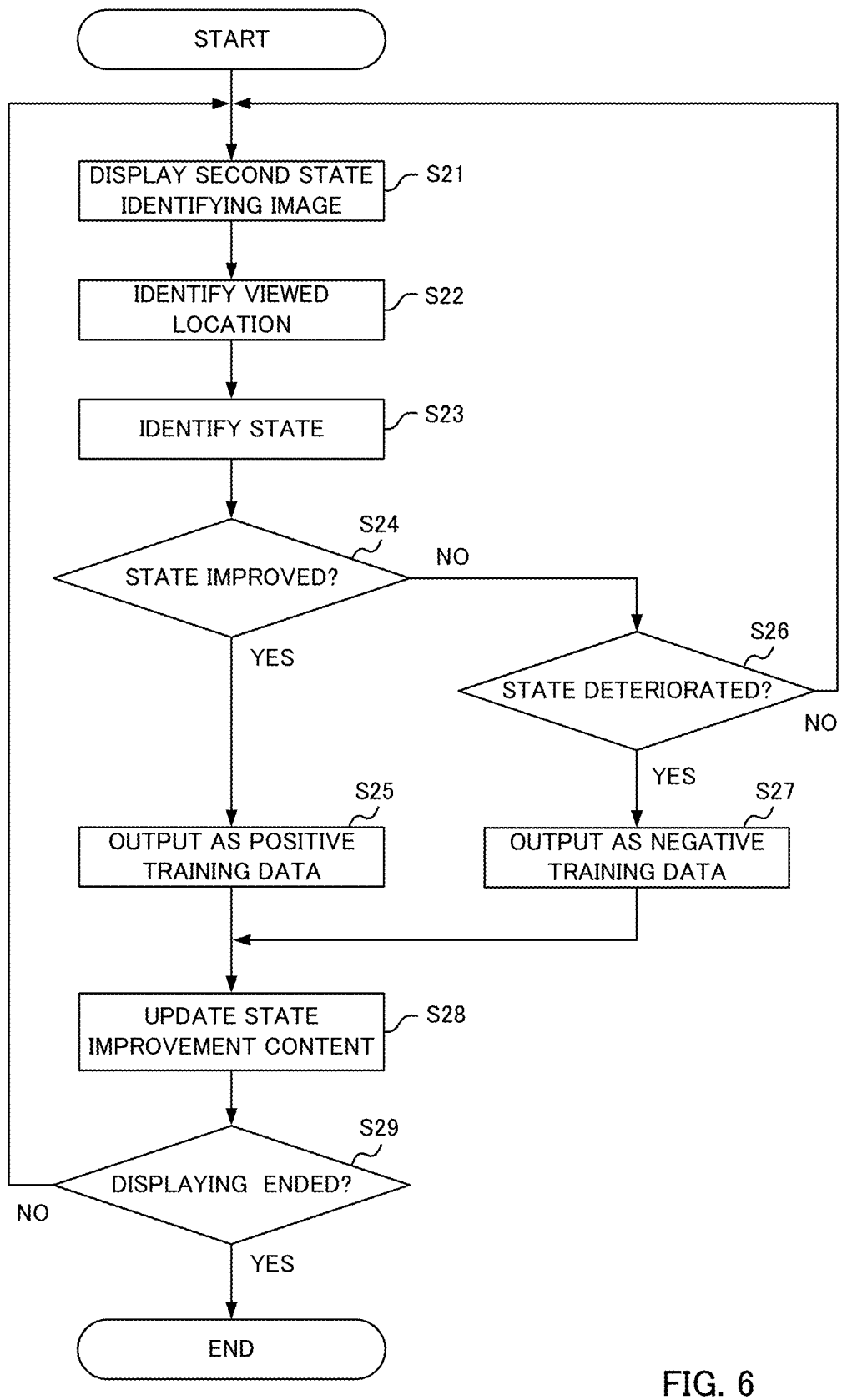
FIG. 6 is a flowchart showing a flow of processing in which the content display apparatus 1 updates the state improvement content.

FIG. 6 is a flowchart showing the flow of processing in which the content display apparatus 1 updates state improvement content. The flowchart shown in FIG. 6 starts from a state where the display control part 155 causes the display part 11 to display the state improvement content. After causing the state improvement content to be displayed, the display control part 155 causes the display part 11 to display the second state identifying image (S21). The viewed location identifying part 152 identifies the viewed location of the viewer U viewing the second state identifying image (S22).

On the basis of the viewed location identified by the viewed location identifying part 152 (S23), the state identifying part 153 identifies the state of the viewer U, and determines whether or not the state has been improved by comparing the state before the viewer U viewed the state improvement content with the state after the viewer U viewed the state improvement content (S24).

If it is determined that the state has been improved (YES in S24), the state identifying part 153 outputs data indicating a relationship between the state of the viewer U before the viewer U viewed the state improvement content and the state improvement content viewed by the viewer U, as positive training data used as positive data in deep learning (S25). The state identifying part 153 may output data indicating a relationship among the state of the viewer U before the viewer U viewed the state improvement content, content of the plurality of pieces of image data included in the state improvement content viewed by the viewer U, and the order and length of the plurality of pieces of image data, as positive training data.

If it is determined that there is no improvement in the state (NO in S24), the state identifying part 153 determines whether or not the state has deteriorated (S26). If it is determined that the state has deteriorated (YES in S26), the state identifying part 153 outputs data indicating the relationship between the state of the viewer U before the viewer U viewed the state improvement content and the state improvement content viewed by the viewer U, as negative training data used as negative data in deep learning (S27). The state identifying part 153 may output data indicating the relationship among the state of the viewer U before the viewer U viewed the state improvement content, the content of the plurality of pieces of image data included in the state improvement content viewed by the viewer U, and the order and the length of the plurality of pieces of image data, as negative training data.

If the state identifying part 153 determines that the state is neither improved nor deteriorated (NO in S26), the content display apparatus 1 returns the processing to S21. If the state identifying part 153 determines that the state has been improved or deteriorated, the generating part 154 updates the state improvement content on the basis of the presence or absence of improvement in the state (S28). If an operation to end displaying the state improvement content has not been performed (NO in S29), the display control part 155 repeats the processing from S21 to S28.

Modified Example

In the above description, a case where the state identifying part 153 identifies the state of the viewer U using biometric information and a viewed location of the viewer U has been exemplified, but the method by which the state identifying part 153 identifies the state of the viewer U is not limited to this, and the state identifying part 153 may identify the state of the viewer U without using biometric information. In this case, the state identifying part 153 identifies the state of the viewer U on the basis of a viewing pattern such as i) the order of locations that the viewer U looks at in the state identifying image, ii) the length of time during which the viewer U looks at a specific location, iii) a range of the viewed location, and iv) a speed at which the viewed location is moved. For example, when the range of the viewed location is narrower than a reference range, the state identifying part 153 determines that the viewer U is possibly in a schizophrenic state.

The state identifying part 153 may identify the state of the viewer U by inputting the viewing pattern of the viewer U to a model created by deep learning using training data in which the viewing pattern and a state of a person are associated with each other in advance. The state identifying part 153 identifies the state of the viewer U on the basis of the viewing pattern in this manner, thereby allowing the state of the viewer U to be identified without having the viewer U wear the biometric information measuring device 2. This makes therapy and identification of the state of the viewer U easier.

The state identifying part 153 may acquire information indicating the state of the viewer U from the outside, instead of using biometric information and a viewed location, and may identify the state of the viewer U on the basis of the acquired information. For example, the state identifying part 153 may acquire information indicating the state of the viewer U identified on the basis of the answer of the viewer U to a plurality of questions (e.g., questions written in questionnaires) prepared in advance for identifying the state, or an interview by a doctor, from an external computer via the communication part 12, and may identify the state of the viewer U on the basis of the acquired information.

Further, in the above description, a case where state improvement content includes image data used as the second state identifying image has been exemplified, but the state improvement content need not include the image data used as the second state identifying image. In this case, the content display apparatus 1 may display the second state identifying image in response to a predetermined operation being performed after the viewer U viewed the state improvement content.

Further, in the above description, the content display apparatus 1 is a goggle device, but the mode of the content display apparatus 1 is any mode. The content display apparatus 1 may be implemented by a smartphone that executes predetermined application software, for example.

Further, in the above description, a case where biometric information of the viewer U is acquired by having the viewer U wear the biometric information measuring device 2 on his/her wrist has been exemplified, but the method of acquiring the biometric information of the viewer U is any method. For example, the content display apparatus 1 may include a function of measuring biometric information, and the content display apparatus 1 may acquire biometric information, such as a pulse, blood pressure, body temperature, and an amount of sweating of the viewer U.

Effect of the Content Display Apparatus 1

As described above, the content display apparatus 1 determines the order in which to display a plurality of pieces of image data selected on the basis of the state of the viewer U, thereby displaying state improvement content for improving the state of the viewer U on the display part 11. The content display apparatus 1 displaying such state improvement content causes the viewer U having a health problem, such as a mental disorder, to view the state improvement content, thereby improving the state of the viewer U. Such a content display apparatus 1 is suitable as an apparatus for providing digital medicine for a patient with a mental disorder.

The present disclosure is explained on the basis of the exemplary embodiments. The technical scope of the present disclosure is not limited to the scope explained in the above embodiments and it is possible to make various changes and modifications within the scope of the disclosure. For example, all or part of the apparatus can be configured with any unit which is functionally or physically dispersed or integrated. Further, new exemplary embodiments generated by arbitrary combinations of them are included in the exemplary embodiments. Further, effects of the new exemplary embodiments brought by the combinations also have the effects of the original exemplary embodiments.

What is claimed is:

1. A content display apparatus for displaying content, the content display apparatus comprising: 1.
   a state identifying part that identifies a state of a viewer who is to view the content;
   an image data selecting part that selects a plurality of pieces of image data from a plurality of image data candidates on the basis of the state of the viewer identified by the state identifying part;
   a content generating part that generates state improvement content for improving the state of the viewer by determining an order in which to display the plurality of pieces of image data; and
   a display control part that causes a display part viewed by the viewer to display the state improvement content, wherein
   the state identifying part outputs, as training data, i) the state of the viewer identified by the state identifying part, ii) order of a plurality of pieces of image data in the state improvement content viewed by the viewer, and iii) information indicating the presence or absence of a therapeutic effect produced by having the viewer view this state improvement content, to a machine learning model to perform deep learning with the training data, and
   the content generating part obtains the state improvement content output from the machine learning model, wherein the machine learning model outputs the plurality of pieces of image data selected from the plurality of image data candidates arranged in time series.

2. The content display apparatus according to claim 1, wherein
   the content generating part determines a time length of each of the plurality of pieces of image data on the basis of the state of the viewer.

3. The content display apparatus according to claim 2, wherein
   when the viewer is in a nervous state, the content generating part determines to use a first time portion of image data that can relax the viewer as first image data, uses a second time portion of image data that attracts the viewer's interest as second image data, and arranges the first image data after the second image data to generate the state improvement content.

4. The content display apparatus according to claim 1, wherein
   the display control part causes the display part to display a first state identifying image for identifying the state of the viewer before causing the display part to display the state improvement content, and
   the state identifying part identifies the state of the viewer on the basis of a viewed location that is a location that the viewer is looking at in the first state identifying image.

5. The content display apparatus according to claim 4, wherein
   the state identifying part identifies the state of the viewer on the basis of content of an image displayed at the viewed location.

6. The content display apparatus according to claim 4, wherein
   the content display apparatus further includes a biometric information acquiring part that acquires biometric information of the viewer while the viewer is looking at the first state identifying image, wherein
   the state identifying part identifies the state of the viewer on the basis of a relationship between the viewed location and the biometric information acquired by the biometric information acquiring part, at the time when the viewer is viewing this viewed location.

7. The content display apparatus according to claim 4, wherein
   the content generating part generates the state improvement content including image data used as a second state identifying image for identifying the state of the viewer, and
   the state identifying part identifies the state of the viewer on the basis of a viewed location that is a location being looked at in the second state identifying image.

8. The content display apparatus according to claim 7, wherein
   the state identifying part identifies a result of comparing a first state of the viewer identified on the basis of a result of the viewer viewing the first state identifying image with a second state of the viewer identified on the basis of a result of the viewer viewing the second state identifying image, and
   the content generating part generates second state improvement content to be displayed, caused by the display control part, on the display part after first state improvement content, on the basis of a result of comparison by the state identifying part.

9. The content display apparatus according to claim 8, wherein
   if the state identifying part determines that a therapeutic effect is not produced on the basis of the result of the comparison, the content generating part generates the second state improvement content including a plurality of pieces of image data that may be able to improve the state of the viewer and is different from a plurality of pieces of image data included in the first state improvement content looked at by the viewer.

10. The content display apparatus according to claim 8, wherein
if the state identifying part determines that a therapeutic effect is not produced on the basis of the result of the comparison, the content generating part generates the second state improvement content in which a plurality of pieces of image data included in the first state improvement content are included in a different order or with a different length than in the first state improvement content.

11. The content display apparatus according to claim 8, wherein
if the state identifying part determines that an adverse effect is produced, the content generating part generates the second state improvement content including a plurality of pieces of image data associated with an attribute different from an attribute of the viewer, among other image data that may be useful for improving the state of the viewer.

12. The content display apparatus according to claim 8, wherein
if the state identifying part determines that a therapeutic effect is produced on the basis of the result of the comparison, the content generating part generates the second state improvement content in which a plurality of pieces of image data that are the same as the first state improvement content or included in the first state improvement content are included, in a different order or with a different length than in the first state improvement content.

13. The content display apparatus according to claim 7, wherein
the display control part causes the display part to display the state improvement content including a plurality of pieces of image data used for therapy for the viewer for a predetermined time required to change the state of the viewer, and then causes the display part to display the second state identifying image.

14. The content display apparatus according to claim 1, wherein
when the state of the viewer is input, the image data selecting part inputs the state of the viewer identified by the state identifying part to a machine learning model that outputs the plurality of pieces of image data selected from the plurality of image data candidates, and selects the plurality of pieces of image data output from the machine learning model.

15. The content display apparatus according to claim 1, wherein
when the state of the viewer is input, the content generating part inputs the state of the viewer identified by the state identifying part to a machine learning model that outputs the state improvement content in which the plurality of pieces of image data selected from the plurality of image data candidates are arranged, and generates the state improvement content output from the machine learning model.

16. The content display apparatus according to claim 1, wherein
the content display apparatus includes a generating part that functions as the image data selecting part and the content generating part, and
when the state of the viewer is input, the generating part generates the state improvement content by inputting the state of the viewer identified by the state identifying part to a machine learning model that outputs the state improvement content in which the plurality of pieces of image data selected from the plurality of image data candidates are arranged.

17. A content display method, executed by a computer, comprising the steps of:
identifying a state of a viewer who is to view content using a content display apparatus;
selecting a plurality of pieces of image data from a plurality of image data candidates on the basis of the identified state of the viewer;
generating state improvement content for improving the state of the viewer by determining an order in which to display the plurality of pieces of image data; and
causing a display part viewed by the viewer to display the content, wherein
the identifying the state of the viewer includes outputting to a machine learning model, as training data, i) the state of the viewer, ii) order of a plurality of pieces of image data in the state improvement content viewed by the viewer, and iii) information indicating the presence or absence of a therapeutic effect produced by having the viewer view this state improvement content, for performing deep learning with the training data, and
the generating state improvement content obtains the state improvement content output from the machine learning model, wherein the machine learning model outputs the plurality of pieces of image data selected from the plurality of image data candidates arranged in time series.

18. A non-transitory storage medium storing a program for causing a computer to function as:
a state identifying part that identifies a state of a viewer who is to view content using a content display apparatus;
an image data selecting part that selects a plurality of pieces of image data from a plurality of image data candidates on the basis of the state of the viewer identified by the state identifying part;
a content generating part that generates state improvement content for improving the state of the viewer by determining an order in which to display the plurality of pieces of image data; and
a display control part that causes a display part viewed by the viewer to display the state improvement content, wherein
the state identifying part outputs, as training data, i) the state of the viewer identified by the state identifying part, ii) order of a plurality of pieces of image data in the state improvement content viewed by the viewer, and iii) information indicating the presence or absence of a therapeutic effect produced by having the viewer view this state improvement content, to a machine learning model to perform deep learning with the training data, and
the content generating part obtains the state improvement content output from the machine learning model, wherein the machine learning model outputs the plurality of pieces of image data selected from the plurality of image data candidates arranged in time series.

19. The content display apparatus according to claim 1, wherein
the training data is further be associated with the attributes of the viewer, and
the state of the viewer includes an attribute of the viewer.

20. The content display method according to claim 17, wherein
    the outputting the training data by the computer further includes outputting training data associated with the attributes of the viewer, and
    the identifying the state of the view includes identifying an attribute of the viewer.

21. The content display apparatus according to claim 1, wherein the content generating part obtains the state improvement content output from the machine learning model by inputting the state of the viewer identified by the state identifying part.

* * * * *